United States Patent
Wicks et al.

(10) Patent No.: US 11,230,702 B2
(45) Date of Patent: Jan. 25, 2022

(54) BLOOD BRAIN BARRIER MODEL AND METHODS OF MAKING AND USING THE SAME

(71) Applicant: WAKE FOREST UNIVERSITY HEALTH SCIENCES, Winston-Salem, NC (US)

(72) Inventors: Robert T. Wicks, Clemmons, NC (US); Anthony Atala, Winston-Salem, NC (US); Goodwell Nzou, Winston-Salem, NC (US); Elizabeth E. Wicks, Ocean Springs, MS (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 100 days.

(21) Appl. No.: 16/322,232

(22) PCT Filed: Aug. 4, 2017

(86) PCT No.: PCT/US2017/045458
§ 371 (c)(1),
(2) Date: Jan. 31, 2019

(87) PCT Pub. No.: WO2018/027112
PCT Pub. Date: Feb. 8, 2018

(65) Prior Publication Data
US 2019/0194625 A1 Jun. 27, 2019

Related U.S. Application Data

(60) Provisional application No. 62/370,907, filed on Aug. 4, 2016, provisional application No. 62/524,877, filed on Jun. 26, 2017.

(51) Int. Cl.
*C12N 5/071* (2010.01)
*C12N 5/00* (2006.01)

(52) U.S. Cl.
CPC ......... *C12N 5/0697* (2013.01); *C12N 5/0062* (2013.01); *C12N 5/0691* (2013.01); *C12N 2502/081* (2013.01); *C12N 2502/086* (2013.01); *C12N 2502/28* (2013.01); *C12N 2506/45* (2013.01); *C12N 2513/00* (2013.01); *C12N 2533/54* (2013.01); *C12N 2537/10* (2013.01)

(58) Field of Classification Search
CPC .. C12N 5/0697; C12N 5/0691; C12N 5/0062; C12N 2502/081; C12N 2502/086; C12N 2502/28; C12N 2506/45; C12N 2513/00; C12N 2533/54; C12N 2537/10; C12N 5/0619; C12M 23/16; G01N 33/5058
See application file for complete search history.

(56) References Cited

U.S. PATENT DOCUMENTS

| | | | |
|---|---|---|---|
| 7,051,654 B2 | 5/2006 | Boland et al. | |
| 7,731,988 B2 | 6/2010 | Thomas et al. | |
| 8,409,624 B2 | 4/2013 | Doi et al. | |
| 8,691,279 B2 | 4/2014 | Guillen et al. | |
| 8,754,564 B2 | 6/2014 | Bennett et al. | |
| 8,808,730 B2 | 8/2014 | Ratcliffe | |
| 8,815,277 B2 | 8/2014 | Park et al. | |
| 9,506,039 B2 | 11/2016 | Yamanaka et al. | |
| 2009/0208466 A1 | 8/2009 | James et al. | |
| 2010/0021437 A1 | 1/2010 | Isacson et al. | |
| 2011/0053207 A1 | 3/2011 | Hoganson et al. | |
| 2012/0015395 A1 | 1/2012 | Shusta et al. | |
| 2012/0089238 A1 | 4/2012 | Kang et al. | |
| 2014/0038279 A1 | 2/2014 | Ingber et al. | |
| 2014/0127800 A1* | 5/2014 | Shusta | C12N 5/069 435/347 |
| 2014/0206028 A1 | 7/2014 | Hickman et al. | |
| 2017/0370908 A1* | 12/2017 | Dauth | C12N 5/0697 |
| 2018/0298331 A1 | 10/2018 | Kerns et al. | |

FOREIGN PATENT DOCUMENTS

| | | |
|---|---|---|
| WO | 2016/100695 | 6/2016 |
| WO | 2017/143049 | 8/2017 |

OTHER PUBLICATIONS

Lippman et al. "A retinoic acid-enhanced, multicellular human blood-brain barrier model derived from stem cell sources." Sci Rep. Feb. 24, 2014;4:4160. (Year: 2014).*

Eigenmann et al. "Comparative study of four immortalized human brain capillary endothelial cell lines, hCMEC/D3, hBMEC, TY10, and BB19, and optimization of culture conditions, for an in vitro blood-brain barrier model for drug permeability studies." Fluids Barriers CNS. Nov. 22, 2013;10(1):33. (Year: 2013).*

Lippmann et al. "Blood-brain barrier modeling with co-cultured neural progenitor cell-derived astrocytes and neurons." J. Neurochem. (2011) 119, 507-520. (Year: 2011).*

Herland et al. "Distinct Contributions of Astrocytes and Pericytes to Neuroinflammation Identified in a 3D Human Blood-Brain" PLoS One. Mar. 1, 2016;11(3):e0150360. (Year: 2016).*

3D Human Blood Brain Barrier datasheet by Neuromics, accessed May 1, 2019 from www.neuromics.com, 12 pages.

Ballabh et al., The blood-brain barrier: an overview Structure, regulation, and clinical implications, Neurobiology of Disease, 2004, vol. 16, issue 1, pp. 1-13.

Bhatia and Ingber, Microfluidic organs-on-chips, Nature Biotechnology, 2014, vol. 32, No. 8, pp. 760-772.

Brown et al., Recreating blood-brain barrier physiology and structure on chip: A novel neurovascular microfluidic bioreactor, Biomicrofluidics, 2015;9:054124, pp. 1-15.

(Continued)

*Primary Examiner* — Titilayo Moloye
(74) *Attorney, Agent, or Firm* — Myers Bigel, P.A.

(57) ABSTRACT

Provided herein is an in vitro model of the blood brain barrier. In some embodiments, the model includes: an endothelial cell layer, and brain tissue layer comprising neuronal cells, and optionally one or more of astrocytes, pericytes, oligodendrocytes, and microglia. In some embodiments, the model further comprises a porous membrane between said endothelial cell layer and the neuronal cell layer. A microfluidic device comprising the same and methods of use thereof are also provided.

24 Claims, 7 Drawing Sheets

(56) References Cited

OTHER PUBLICATIONS

Cho et al., Blood-brain-barrier spheroids as an in vitro screening platform for brain-penetrating agents, Nature Communications, vol. 8, 2017, pp. 1-14.
Etame et al., Focused ultrasound disruption of the blood brain barrier: a new frontier for therapeutic delivery in molecular neuro-oncology, Neurosurg Focus, 2014, vol. 32, Issue 1, pp. 1-17.
Kang et al., A 3D bioprinting system to produce human-scale tissue constructs with structural integrity, Nature Biotechnology, vol. 34, 2016, pp. 312-319, with Online Methods (3 pages).
Kimbrough et al., Vascular amyloidosis impairs the gliovasular unit in a mouse model of Alzheimers disease, Brain A Journal of Neurology, 2015, vol. 138, Issue 12, pp. 3716-3733.
Lancaster et al, Cerebral organoids model human brain development and microcephaly, Nature, 2013, 501(7467), pp. 373-379.
Naik et al., In Vitro Blood-Brain Barrier Models: Current and Perspective Technologies, J Pharm Sci., 2012, vol. 101, Issue 4, pp. 1337-1354.
Nzou et al., Human Cortex Spheroid with a Functional Blood Brain Barrier for High-Throughput Neurotoxicity Screening and Disease Modeling, Scientific Reports, vol. 8, 2018, pp. 1-10.
Pamies et al, A Human Brain Microphysiological System Derived from Induced Pluripotent Stem Cells to Study Neurological Diseases and Toxicity, ALTEX, 2017, vol. 34, Issue 3, pp. 362-376.
Spampinato et al, Astrocytes contribute to AB-induced blood-brain barrier damage through activation of endothelial MMP9, Journal of Neurochemistry, 2017, vol. 142, pp. 464-477.
Talan, J., A Novel Brain Model Replicates Six Cell Types and a Functioning Blood-Brain Barrier, American Academ Neurology, Aug. 2, 2018, pp. 13-15.
Wake Forest Institute for Regenerative Medicine (WFIRM), "Wake Forest Researchers Create Advanced Brain Organoid to Model Strokes, Screen Drugs." published May 30, 2018, accessed May 1, 2019, 3 pages.
Written Opinion corresponding to International Patent Application No. PCT/US2017/045458, dated Oct. 19, 2017, 4 pages.
Urich et al. "Multicellular Self-Assembled Spheroidal Model of the Blood Brain Barrier" Scientific Reports, 3(1): 8 pp (2013).
Lippmann et al. "A retinoic acid-enhanced, multicellular human blood-brain barrier model derived from stem cell sources" Scientific Reports, 4(1): 10 pp (2014).
Extended European Search Report corresponding to EP17837743.8; dated Dec. 11, 2019 (11 pp).
Terasaki, T et al. "New approaches to in vitro models of blood-brain barrier drug transport" Drug Discovery Today, 8:(20)944-954 (2003).
Zozulya, A et al. "Pericyte-endothelial cell interaction increases MMP-9 secretion at the blood-brain barrier in vitro" Brain Research, 1189:1-11 (2007) Abstact.
Written Opinion and International Search Report corresponding to International Patent Application No. PCT/US2017/045458, dated Oct. 19, 2017, 7 pages.
European Examination Report corresponding to 17837743.8; dated Apr. 23, 2021 (6 pages).
Japanese Office Action corresponding to JP 2019-505398; dated Jul. 13, 2021 (11 pages, including English translation).
Eigenmann, Daniela E., et al., "Comparative study of four immortalized human brain capillary endothelial cell lines, hCMEC/D3, hBMEC, TY10, and BB19, and optimization of culture conditions, for an in vitro blood-brain barrier model for drug permeability studies", Fluids and Barriers of the CNS 10(1), 2013, Article No. 33.
Herland, Anna , et al., "Distinct Contributions of Astrocytes and Pericytes to Neuroinflammation Identified in a 3D Human Blood-Brain Barrier on a Chip", PLOS ONE 11(3), 2016, e0150360.
Korean Office Action corresponding to KR 10-2019-7006450; dated Oct. 18, 2021 (10 pages, including English translation).

\* cited by examiner

CALCEIN AM / ETHD-1

B  D14

CALCEIN AM / ETHD-1

C  D30

30μm
CALCEIN AM / ETHD-1

D  D30

40μm
BETA III TUBULIN / DAPI

BLOOD BRAIN BARRIER MODEL AND METHODS OF MAKING AND USING THE SAME

RELATED APPLICATIONS

This application claims the benefit of U.S. Provisional Patent Application Ser. No. 62/370,907, filed Aug. 4, 2016, and U.S. Provisional Patent Application Ser. No. 62/524,877, filed Jun. 26, 2017, the disclosures of each of which are incorporated herein by reference in their entirety.

BACKGROUND

The blood brain barrier (BBB) is a dynamic component of the brain that prevents entry of foreign substances into the brain. Ballabh et al. *The blood-brain barrier: an overview: structure, regulation, and clinical implications*. Neurobiol Dis. 2004; 16(1):1-13: Hence, the BBB limits therapeutic options for many neurologic diseases and disorders.

Techniques such as focused ultrasound and certain drugs have been researched to overcome this limitation, Etame et al. *Focused ultrasound disruption of the blood-brain barrier: a new frontier Or therapeutic delivery in molecular neurooncology*. Neurosurg Focus, 2012, 32(1):E3. However, currently, very little is known about the mechanisms that govern the dynamic nature of the BBB. In vitro and animal models fail to recapitulate the physiological nature of the adult human BBB and/or are not designed to allow for high-throughput trials. Naik et al. *In vitro blood-brain barrier models: current and perspective technologies*, J Pharm Sci. 2012; 101(4):1337-54; Lancaster et al., *Cerebral organoids model human brain development and microcephaly*. Nature, 2013, 501(7467): p. 373-9.

Furthermore, in viva animal models also do not always mimic human pathology. Failure of about 90% of the drugs in clinical trials after extensive animal testing could be attributed to the limitations in the current models.

Thus, there remains a need for improved in vitro systems that can be used for study and testing related to the blood brain barrier and human brain tissue.

SUMMARY

Provided herein is an in vitro model of the blood brain barrier. In some embodiments, the model includes: an endothelial cell layer, and brain tissue layer (or neuronal cell layer, these terms being used interchangeably herein to refer to a layer comprising neuronal cells) comprising neuronal cells, and optionally one or more of astrocytes, pericytes, oligodendrocytes, and microglia. In some embodiments, the model further comprises a porous membrane between said endothelial cell layer (e.g., an endothelial cell monolayer) and the neuronal cell layer.

In some embodiments, the neuronal cells comprise primary neuronal cells, neuronal progenitor cells, and/or iPSC-derived cells. In some embodiments, the endothelial cells comprise primary endothelial cells (e.g., primary brain microvascular endothelial cells) or endothelial progenitor cells. In some embodiments, the astrocytes, comprise primary astrocytes, astrocyte progenitor cells and/or iPSC-derived astrocytes. In some embodiments, the pericytes comprise primary pericytes or pericyte progenitor cells. In some embodiments, the neuronal cells, endothelial cells, astrocytes and/or pericytes are human cells.

In some embodiments, the oligodendrocytes comprise primary oligodendrocytes or oligodendrocyte progenitor cells. In some embodiments, the microglia comprise primary microglia or microglia progenitor cells. In some embodiments, the oligodendrocytes and/or microglia are human cells.

In some embodiments, the endothelial cell layer is provided in the shape of a blood vessel, i.e., tubular, with a hollow center to allow liquid flow therethrough. In some embodiments, the neuronal cell layer is situated on the outside of the tubular blood vessel construct.

Also provided is a microfluidic device comprising the in vitro model of the blood brain barrier as taught herein, wherein the endothelial cell layer is in fluid connection with a liquid (e.g., media, a buffer, blood or a fraction thereof, artificial blood substitute, etc.).

In some embodiments, the neuronal cell layer is in fluid connection with a liquid (e.g., media, a buffer, artificial cerebrospinal fluid, etc.), and optionally wherein said liquid is different from the liquid in the fluid connection with the endothelial cell layer.

BRIEF DESCRIPTION OF THE DRAWINGS

FIGS. 4A-4C present schematics of bioprinted structures, and show human primary cells utilized.

DETAILED DESCRIPTION OF EMBODIMENTS

The present invention is now described more fully hereinafter. This invention may, however, be embodied in many different forms, and should not be construed as limited to the embodiments set forth herein; rather, these embodiments are provided so that this disclosure will be thorough and complete and will fully convey the scope of the invention to those skilled in the art.

The terminology used herein is for the purpose of describing particular embodiments only and is not intended to be limiting of the invention. As used herein, the singular forms "a," "an" and "the" are intended to include plural forms as well, unless the context clearly indicates otherwise. It will be further understood that the terms "comprises" or "comprising," when used in this specification, specify the presence of stated features, integers, steps, operations, elements components and/or groups or combinations thereof, but do not preclude the presence or addition of one or more other features, integers, steps, operations, elements, components and/or groups or combinations thereof.

As used herein, the term "and/or" includes any and, all possible combinations or one or more of the associated listed items, as well as the lack of combinations when interpreted in the alternative ("or").

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and claims and should not be interpreted in an idealized or overly formal sense unless expressly so defined herein. Well-known functions or constructions may not be described in detail for brevity and/or clarity.

"Mammalian" as used herein refers to both human subjects (and cells sources) and non-human subjects (and cell sources or types), such as dog, cat, mouse, monkey, etc. (e.g., for research or veterinary purposes).

"Cells" as used herein are, in general, mammalian cells, such as dog, cat, cow, goat, horse, sheep, mouse, rabbit, rat, etc. cells. In some preferred embodiments the cells are human cells. Suitable cells are known and are commercially available, and/or may be produced in accordance with known techniques. In some embodiments, the cells are harvested from a donor and passaged.

"Organoid" as used herein refers to an artificial, in vitro three-dimensional construct created to mimic or resemble the functionality and/or histological structure of an organ or portion thereof.

"Media" as used herein may be any natural or artificial growth media (typically an aqueous liquid) conditioned with supplements and growth factors that sustains the cells used in carrying out the present invention. Examples include, but are not limited to, an essential media or minimal essential media (MEM), or variations thereof such as Eagle's minimal essential medium (EMEM) and Dulbecco's modified Eagle medium (DMEM), and an endothelial growth medium (EGM). Other fluids useful in the present invention include buffers, blood, blood serum, blood plasma, lymph fluid, cerebrospinal fluid, etc., including synthetic mimics thereof. See, e.g., U.S. Pat. No. 8,409,624 to Doi et al. In some embodiments, the growth media, buffer, etc., includes a pH color indicator (e.g., I, phenol red) and/or supplements (e.g., serum, F-12), etc.

The disclosures of all United States patent references cited herein are to be incorporated by reference herein in their entireties.

1. Blood, Brain Barrier Models and Methods of Making the Same.

Provided herein is an in vitro blood brain barrier model, and in some embodiments the model has an endothelial cell layer including one or more of astrocytes, pericytes and endothelial cells. In some embodiments, the endothelial cell layer comprises an organoid, such as a self-assembled organoid of astrocytes, pericytes, endothelial cells (e.g., brain microvascular endothelial cells). In some embodiments, the model further includes a neuronal cell layer comprising neuronal cells. In some embodiments, the model has a porous membrane between the endothelial cell layer and the neuronal cell layer.

In some embodiments, the model includes endothelial cells, astrocytes, and pericytes. In some embodiments, the model further includes a brain tissue layer (or neuronal cell layer, these terms being used interchangeably herein to refer to a layer comprising neuronal cells) comprising neuronal cells. In some embodiments, the neuronal cells are electrically active. See, e.g., U.S. Patent Application Publication No. 2014/0206028 to Hickman et al.

Also provided is an in vitro model of the blood brain barrier including: an endothelial cell layer, and brain tissue layer (or neuronal layer) comprising neuronal cells, and optionally also one or more of astrocytes, pericytes, oligodendrocytes, and microglia. In some embodiments, the model further comprises a porous membrane between said endothelial cell layer (e.g., an endothelial cell monolayer) and the neuronal cell layer.

In some embodiments, in vitro blood brain barrier models of the invention may be made by: depositing an endothelial cell layer (e.g., comprising a self-assembled orgainoid astrocytes, pericytes and endothelial cells) on a porous membrane; and depositing a neuronal cell layer comprising live mammalian neuronal cells on an opposite side of the porous membrane.

In some embodiments, in vitro blood brain barrier models of the invention may be made by: adding brain microvascular endothelial cells and pericytes to organoids containing astrocytes, microglia, oligodendrocytes and neurons. In some embodiments, in vitro blood barrier models of the invention are made by adding endothelial cells onto a hydrogel comprising cells. The cells loaded into the hydrogel may include one or more of pericytes, astrocytes, microglia, oligodendrocytes and neurons.

In some embodiments, the in vitro blood brain barrier model is provided in a tubular shape to mimic a blood vessel. In some embodiments, microvascular endothelial cells may be perfused into the lumen after formation of the vessel shape. In some embodiments, the endothelial cells may be provided in a sacrificial hydrogel and applied (e.g., bioprinted) in the interior of the vessel. The sacrificial hydrogel (e.g., gelatin) may then dissolve in media under growth conditions, allowing the endothelial cells to adhere to the lumen. In some embodiments, the porous membrane (when present) is provided in a tubular shape.

Cells may be obtained from established cultures, donors, biopsy, or a combination thereof in some embodiments, cells are stem cells or progenitor cells (e.g., induced pluripotent stem cells (iPSCs)). In some embodiments, cells are primary cells. In some embodiments, cells are human cells. In some embodiments, cells are iPSC-derived cells (e.g., iPSC-derived astrocytes, iPSC-derived neural stem cells, etc.). In some embodiments, cells are passaged.

Depositing or seeding of the cells can be carried out by any suitable technique, including but not limited to spreading/painting, coating, spraying, etc. In some embodiments the depositing steps are carried out by printing (or "bioprinting") in accordance with any suitable technique, including both "ink jet" type printing and syringe injection type printing. Apparatus for carrying out such bioprinting is known and described in, for example, Boland et al., U.S. Pat. No. 7,051,654; Yon et al., US Patent Application Pub. No. US 2009/0208466; and Kang et al., US Patent Application Publication No. US 2012/0089238.

In some embodiments, cells may be provided and/or bioprinted in a carrier such as a hydrogel carrier. "Hydrogel," as used herein, may be any suitable hydrogel. In general, the hydrogel includes water and is further comprised of or derived from polyalkylene oxides, poloxamines, celluloses, hydroxyalkylated celluloses, polypeptides, polysaccharides, carbohydrates, proteins, copolymers thereof, or combinations thereof, and more particularly are comprised of or derived from polyethylene glycol), polyethylene oxide), poly(vinyl alcohol), poly(vinylpyrrolidone), poly (ethyloxazoline), poly(ethylene oxide)-co-polypropylene oxide) block copolymers, carboxymethyl cellulose, hydroxyethyl cellulose, methylhydroxypropyl cellulose, polysucrose, hyaluronic acid, dextran, heparan sulfate, chondroitin sulfate, heparin, alginate, gelatin, collagen, albumin, ovalbumin, copolymers thereof, or a combination thereof, all of which are preferably cross-linked to varying degrees in accordance with known techniques, or variations thereof that are apparent to those skilled in the art. See, e.g., U.S. Pat. Nos. 8,815,277; 8,808,730; 8,754,564; 8,691,279. In some embodiments, the hydrogel comprises fibrin, which hydrogel may be crosslinked upon printing with thrombin. In some embodiments the hydrogel may comprise mammalian or human brain derived extracellular matrix.

In some embodiments, the hydrogel is a "sacrificial" hydrogel, in that it may be liquefied, solubilized, or otherwise removed after printing, e.g., to form a hollow space within the printed construct. Examples of sacrificial hydrogels include, but are not limited to, those containing sugars, gelatins, salts, low molecular weight water-soluble polymers, biodegradable polymers, and combinations thereof. See, e.g., U.S. Pat. No. 7,731,988 to Thomas et al.

In some embodiments, brain microvascular endothelial cells (e.g., human brain microvascular endothelial cells) and/or brain pericytes (e.g., human brain microvascular pericytes) are provided in a sacrificial hydrogel, which hydrogel is then removed to form a defined lumen surrounded by said cells in the blood brain barrier construct.

As noted above, in some embodiments, a porous membrane may be positioned between the endothelial cell layer and the neuronal cell layer of the model. The porous membrane may be or comprise a polymeric material. The polymeric material may be synthetic, such as polystyrene, or derived from a natural tissue, such as a decelluarized extracellular matrix. In some embodiments, the membrane is coated on one or both sides with collagen, laminin, proteoglycan, vitronectin, fibronectin, poly-D-lysine and/or polysaccharide.

In other embodiments, the in vitro blood brain barrier model does not comprise a porous membrane.

In some embodiments, the model may be provided in a microfluidic device. Various microfluidic device configurations useful for the support of cells, including in the form of in vitro blood vessel models, are known in the art. See, e.g., US 2011/0053207 To Hoganson et al.; US 2014/0038279 to Ingber et al.; Bhatia and Ingber, "Microfluidic organs-on-chips," Nature Biotechnology 32:760-772 (2014), which are incorporated by reference herein.

In general, a microfluidic device comprising the blood brain barrier model as taught herein may comprise a chamber so dimensioned to accept the blood brain barrier model therein such that the endothelial cell layer and neuronal cell layer define a boundary between a first chamber or opening in fluid contact with the endothelial cell layer of the model, and a second chamber or opening in fluid contact with the neuronal cell layer of the model. The fluid may be a liquid such as a media or a buffer. The device may further comprise a fluid inlet and fluid outlet for each chamber, fluid reservoirs (e.g., media reservoirs) connected therewith, etc.

In some embodiments, the blood brain barrier model as taught herein may comprise a lumen so dimensioned to allow fluid flow therethrough (e.g., microfluidic fluid flow therethrough), providing shear stress to endothelial cell layer and enhancing the formation of the blood brain barrier. The fluid is in contact with the endothelial cell layer of the model, and nutrient distribution to the brain tissue is indicated by diffusion and transport mechanisms at the blood brain barrier.

2. Methods of Use.

The in vitro blood brain barrier models as described herein may be used as an alternative to live animal testing for compound or treatment screening or testing (e.g., for efficacy, toxicity, or other metabolic or physiological activity) for pharmacodynamic or pharmacokinetic testing of the passage of agents through the blood brain barrier, etc. Such testing may be carried out by providing an in vitro blood brain barrier model as described herein under conditions which maintain constituent cells of that product alive (e.g., in a culture media with oxygenation); applying a compound to be tested (e.g., a drug candidate) to the cells (e.g., by administration to the endothelial layer); and then detecting a penetration of the compound through the endothelial layer and/or other physiological response (e.g., damage, scar tissue formation, infection, cell proliferation, burn, cell death, marker release such as histamine release, cytokine release, changes in gene expression, etc.), which may indicate whether said compound can penetrate the blood brain barrier and/or has therapeutic efficacy, toxicity, or other metabolic or physiological activity in the brain if systemically delivered (e.g., intravascularly) to a mammalian subject. A control sample of the in vitro blood brain barrier may be maintained under like conditions, to which a control compound (e.g., physiological saline, compound vehicle or carrier) may be applied, so that a comparative result is achieved, or damage can be determined based on comparison to historic data, or comparison to data obtained by application of dilute levels of the test compound, etc.

Methods of determining whether a test compound has immunological activity may include testing for immunoglobulin generation, chemokine generation and cytokine generation by the microglia or astrocytes of the blood brain barrier model or by assessing migration of innate immune cells such as the neutrophils, and macrophages into the neuronal layer.

Methods of crossing the blood brain barrier (e.g., the human blood brain barrier) that may be, tested with the models taught herein include, but are not limited to, assessing permeability of different paracellular tight junctions, passive diffusion through the cell layers, receptor-mediated transcytosis, and/or cell efflux inhibition. See Wicks et al., Chapter 15: Transport of nanoparticles across the blood-brain barrier. NANONEUROSURGERY AND NANONEUROSMNCE (Kateb and Heiss, eds.) New York; Taylor and Francis, 2013.

In some embodiments, the model may be used in personalized testing of a subject (e.g., for efficacy, toxicity, or other metabolic or physiological activity) for pharmacodynamic or pharmacokinetic testing of the passage of agents through the blood brain barrier, etc., with at least some of the cells of the model being from the subject. For example, fibroblast cells of the subject may be directed to induced pluripotent stem cells (e.g., induced pluripotent neural stem cells), which cells thereafter are directed to one or more cell types for the model, e.g., neuronal cells, oligodendrocytes, endothelial cells, astrocytes, microglia, etc. See, e.g., U.S. Pat. No. 9,506,039 to Yamanaka et al.; U.S. Patent Application Publication No. 2010/0021437.

In some embodiments, the in vitro blood brain barrier model comprises cells with a known genetic mutation that may affect the function of the blood brain barrier, e.g., defects in glucose transporter type 1 (GLUT1), which is known to be a cause of De Vivo disease, and/or cells that express or overexpress certain proteins, such as Aβ1-42, implicated in Alzheimer's disease.

The present invention is explained in greater detail in the following non-limiting Examples.

EXAMPLES

Example 1

We sought to bioprint a reproducible vessel model of the blood brain barrier. A component of this is to print electrically active neuronal cells for the layers surrounding the vascular lumen portion of the model.

Cortical tissue was printed using ReNcellVM human neuro progenitor cell line as a proof of concept. The cells were printed in a hydrogel containing gelatin 35 mg/ml, fibrinogen 10 mg/ml, glycerol 10 mg/ml and hyaluronic acid 10 mg/ml. The hydrogel was crosslinked with 2 mg/ml thrombin immediately after printing. The printed constructs were 1 cm by 1 cm by 300 micrometers. Upon successfully printing viable ReNcell, we then cultured the printed constructs in DMEM/F12 without growth factors (EGF and FGF) to allow the cells to differentiate to a mature population of neurons. After successful differentiation which was confirmed by the expression of Beta III tubulin, we subsequently printed induced pluripotent stem cell—human derived neuronal stem cells in the same hydrogel as above, and cell differentiation was also confirmed by Beta III tubulin expression.

The printed structures were kept in culture for 7 weeks and cell viability was at least 80% over the course of 5 weeks. Cell differentiation in both ReNcells and the iPSc-human derived neuronal stem cells was evident by day 30, confirmed by expression of Beta 3 tubulin, a marker specific to differentiated neurons.

Electrical activity and synapse formation of the neurons in printed constructs may be analyzed. Bioprinted structures containing neuronal stem cells, oligodendrocyte progenitor cells, astrocytes, and microglia may be created.

Example 2

Human Cortex Model with Spheroid Culture System

Increased cerebrovascular permeability due to blood brain barrier (BBB) disruption is known for destabilizing brain homeostasis, neuronal function and nutritional distribution in brain tissue. The BBB controls these functions through a dynamic structure of tight junctions (TJ) and adherens junctions (AJ) formed mainly between endothelial cells. The integral selectivity characteristic of the BBB limits therapeutic options for many neurologic diseases and disorders.

Currently, very little is known about the mechanisms that govern the dynamic nature of BBB. To date, most in vitro models only utilize endothelial cells, pericytes and astrocytes (1-4). See, e.g., Spampinato et al. Astrocytes contribute to AB-induced blood brain barrier damage through activation of endothelial MMP9. J Neurochem. 2017; Parmies et al. A human brain microphysiological system derived from induced pluripotent stem cells to study neurological diseases. ALTEX. 2016 Nov. 24; Brown et al. Recreating blood-brain barrier physiology and structure on chip: a novel neurovascular microfluidic bioreactor. Biomicrofluidics. 2015; 9:054124. These models neglect the role of other cell types in the brain cortex such as the neurons, microglia and oligodendrocytes. Thus, a 3D spheroid model of the blood brain barrier was created with all major cell types to recapitulate normal human brain tissue.

Cell Sourcing and Expansion

Primary human endothelial cells, pericytes, astrocytes, and microglia were utilized. iPSC—derived neuro-progenitor stem cells and oligodendrocyte progenitor cells were utilized. The cells were expanded prior to subsequent use in forming spheroids. Cells used were between passages 4-13.

Spheroid Manufacturing

Endothelial pericytes and astrocytes spheroids were cultured using the hanging drop method in a ratio of 1:1:3 respectively. These were made using 1500 total cells and maintained an average of around 200 microns in diameter. Astrocyte-only spheroids were created for comparison using the same protocol. The specific cell locations in the spheroids were established by pre-staining with cell tracker dyes from ThermoFisher Scientific. Six cell type spheroids consisting of 30% Endothelial cells, 15% pericytes, 15% astrocytes, 15% oligodendrocytes, 5% microglia and 20% neurons were also cultured following the hanging drop protocol and were then grown in 40% Astrocyte media (Sciencell), 30% EGM2 (Lonza) and 30% Neural Maintenance Media XF (Axol Bioscience). Spheroids were maintained in static culture with fresh media exchange every 48 hours.

Spheroid Characterization

Viability of the spheroids was assessed with 2 µM Calcein AM and 4 µM EthD-1 solution. The spheroids were incubated at room temperature in this solution for 15 minutes and then washed with PBS before imaging using FLUOVIEW FV10i (Olympus). Viable spheroids were maintained in static culture for up to 35 days.

The spheroids were fixed in 4% formaldehyde, and immunohistochemistry was performed for TJ, AJ and cell specific markers on day 10 and day 21. Immunohistochemistry was performed for TJ, AJ and cell specific markers targeting cell specific markers following well established whole tissue immunofluorescence staining protocols with adjustments. We will target GFAP marker for astrocytes (5), CD31 for Human brain microvascular endothelial cells (HBMVEC), platelet-derived growth factor receptor-beta (PDGFR) for pericytes (6), ionized calcium-binding adapter molecule 1 (Iba1) for microglia (7), O4 for oligodendrocytes (8) and neuron specific enolase (9) for neurons (10).

Spheroid Results and Significance

The data demonstrated very high cell viability and expression of TJs and AJs in six-cell type spheroids. This spheroid model has applications in drug discovery and neurotoxicity and cytotoxicity testing. This model can also serve as a tool for individualized, patient-specific blood brain barrier disease models through the use of representative cell types derived from induced pluripotent stem cells (iPSCs).

Example 3

Bioprint Functional Cortical Tissue

The bio-printed cortical tissue was simplified to just printing the neurons for this part in order to establish feasibility. Neurons were suspended in a fibrin hydrogel prepared as outlined above and printed using the ITOP3 printing system, Nature Biotech, 2016 March; Kang et al. After a brief incubation period in thrombin to crosslink the fibrinogen, the structures were cultured in ReNcell VM maintenance medium supplemented with GDNF and cAMP. Viability assays were performed at days 7, 14, and 21.

Printed constructs were cultured in differentiation media for up to 70 days. In order to evaluate Beta III tubulin expression—a neuronal differentiation marker, the printed constructs were fixed in 4% Paraformaldehyde for 30 minutes at 4° C., and then incubated overnight in DAKO protein block. After removing the protein block, the primary antibodies (anti Beta III tubulin antibody) was added at a ratio of 1:500 and incubated overnight at 4° C. After washing, the secondary antibodies were added at a concentration of 1:1000 and incubated at 4° C. overnight. Finally, the constructs were stained for DAPI at a concentration of 1:1000 for 30 minutes before imaging and analysis using the Olympus Fluoview FV10i.

Bioprint a micro vessel with all cell types recapitulating the brain parenchyma. Cells used were as follows: human Brain Microvascular Endothelial Cells (hBMECs), primary cells; human brain microvascular pericytes (hP), primary cells; human Astrocytes (hA), primary cells; neurons (iPSC-derived neuronal stem cells-cord blood-CD34+ cells) (hiPSC-NSC); oligodendrocytes—iPSC derived oligodendrocyte progenitor cells) (hiPSC-OPC); human microglia (hM), primary cells. Each cell type was expanded in culture in preparation for 3D bioprinting. A three-dimensional bioprinted microvessel construct was designed and printed containing three cell types: hBMECs, hbMPs, and hAs; and a micro-arteriole NVU containing the three prior cell types with the addition of human Brain Smooth Muscle Cells (hBSMCs) was also formed. A human neurovascular unit design containing all six cell types of the human brain cortex may also printed: containing hBMECs, hBMPs, hAs, hiPSC-NSC, hiPSC-OPC, hM.

Figure 1:
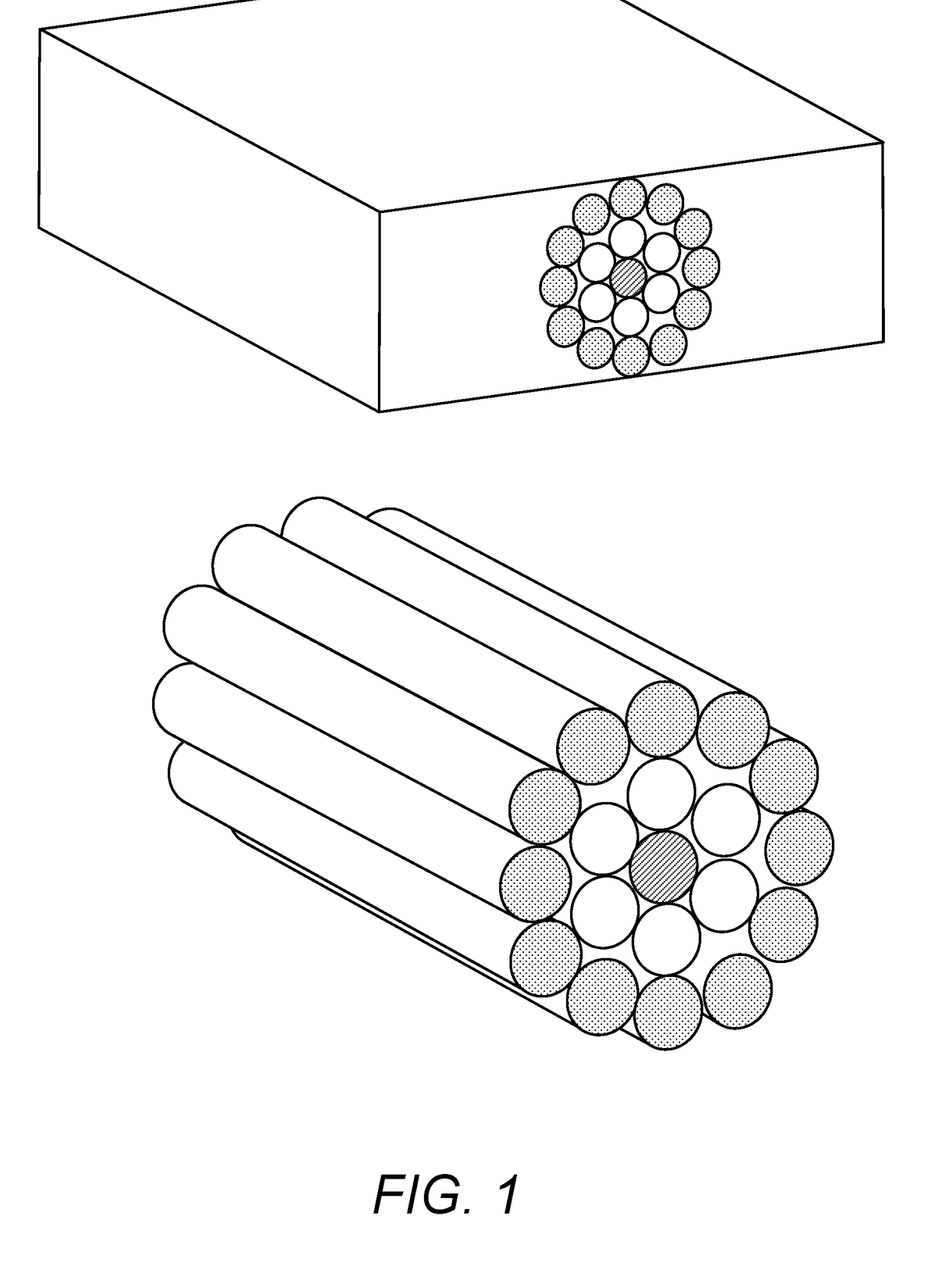
FIG. 1 shows a design of a blood brain barrier vessel model. The middle circle represents the dissolvable lumen with endothelial cells, which is surrounded by astrocytes and pericytes.

FIG. 1 shows a design of a blood brain barrier vessel model. The middle circle represents the dissolvable lumen with endothelial cells, which is surrounded by astrocytes and pericytes.

Figure 2:
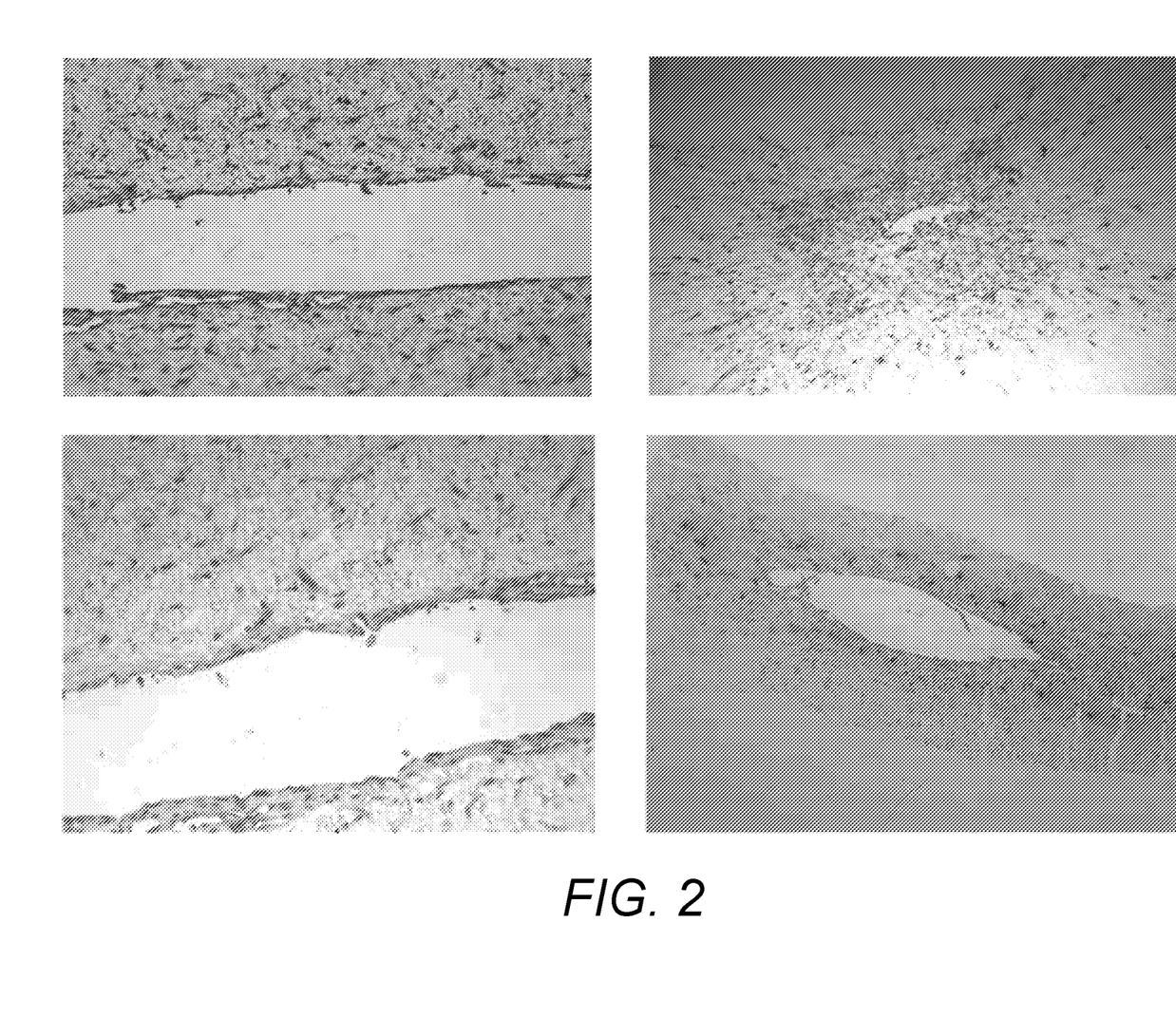
FIG. 2 shows images of bioprinted microvessels. The microvessels were printed in fibrin with smooth muscle cells, endothelial cells, pericytes and astrocytes. Imaging depicts H&E staining of paraffin embedded structures with the predicted lumen evidenced on Day 4 after dissolving of the sacrificial lumen. GFAP staining confirmed the predicted astrocyte location.

FIG. 2 is an image of bioprinted microvessels. The microvessels were printed in fibrin with smooth muscle cells, endothelial cells, pericytes and astrocytes. Imaging depicts H&E staining of paraffin embedded structures with the predicted lumen evidenced on Day 4 after dissolving of the sacrificial lumen, GFAP staining confirmed the predicted astrocyte location.

Isolated primary human cells were acquired for the four cell types utilized in the models. Cells used were between passages 4-13. Spheroids and printed structures were maintained in static culture with growth media exchange every other day. Spheroids and printed structures were fixed in 4% formaldehyde and immunohistochemistry was performed for TJ, AJ and cell specific markers. Viability of the spheroids and printed structure was assessed with 2 μM Calcein AM and 4 μM EthD-1 solution.

Claudin-5, PDGFR, O4, Beta III tubulin, α-SMA, CD31, VE-cadherin, Glut1, synaptophysin, PSD95, GFAP, ZO-1 and MDR-1 expression in the spheroids was confirmed. Claudin-5 and ZO-1 are tight junction markers, MDR-1 is a transport protein that actively transports foreign substances such as drugs out of the brain parenchyma. GFAP, marker for astrocytes was also detected. In order to identify these markers in the spheroids were fixed in 4% Paraformaldehyde for 30 minutes at 4° C. The spheroids were suspended in 0.5% Trypsin for 20 minutes at 4° C. for antigen retrieval. The spheroids were then incubated overnight in DAKO protein block. The respective primary antibodies were then added in a ratio of 1:500 and left overnight at 4° C. as well. After washing the spheroids, the secondary antibodies were added at a concentration of 1:1000 and incubated at 4° C. overnight. The spheroids were stained for DAPI at a concentration of 1:1000 for 30 minutes before imaging using the Olympus Fluoview FV10i.

Viable spheroids were maintained for up to 35 days. The spheroids showed expression of BBB protein markers. Spheroids with all 3 cell types displayed a noticeable difference in integral BBB protein expression compared to monocellular spheroids.

Figure 3:
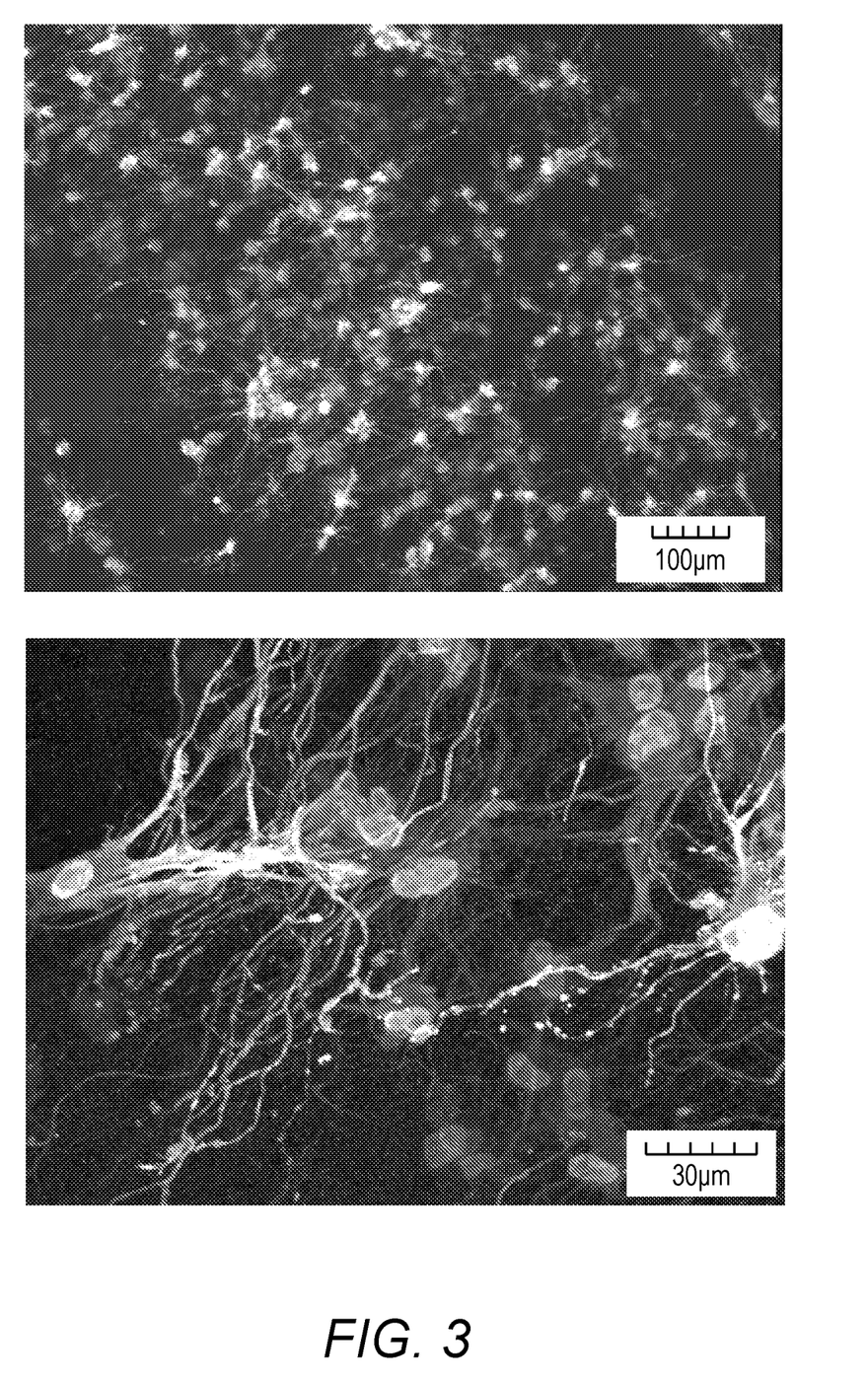
FIG. 3 shows printed neurons that were successfully cultured for more than 8 weeks. The printed neurons differentiated and displayed proper cell morphology.

Printed neurons were successfully cultured for more than 8 weeks. The printed neurons differentiated and displayed proper cell morphology, as shown in FIG. 3.

Example 4

Three-Dimensional Bioprinting of the Human Neurovascular Unit

The BEE controls the barrier functions through a dynamic structure of tight junctions (TJ) and adherens junctions (AJ) formed mainly between endothelial cells. The capillary BBB is composed of the cell types of human brain microvascular endothelial cells (hBMECs), human brain microvascular pericytes (hBMPs), human astrocytes (hAs) and neurons. At the site of microvascular arterioles, human brain smooth muscle cells (hBSMCs) are also present. The organization of these cell types is termed the neurovascular unit (NVU). With the use of three-dimensional bioprinting, we seek to develop a standardized laboratory model of the human NYU with a functional blood brain barrier. This model would have applications in drug discovery and neurotoxicity testing. In addition, with the use of representative cell types derived from induced pluripotent stem cells (iPSCs), individualized, patient-specific blood brain barrier disease models may be feasible.

Four three-dimensional bioprinted NVU Conga/CIS were designed: 1) Cortical tissue with mature neurons and optionally oligodendrocytes, astrocytes, and/or microglia; 2) capillary NVU containing 3 cell types (hBMECs), hBMPs, and hAs; 3) micro-arteriole NVU containing the 3 prier cell types with the addition of hBSMCs, and 4) cortical NYU containing neurons, oligodendrocytes, astrocytes, microglia, pericytes, and brain microvascular endothelial cells. Primary human cells or induced pluripotent stem cell derived cells were utilized in the models. Each cell type was expanded in 2D culture in preparation for 3D bioprinting. Cells used were between passages 4-11.

Figure 4:
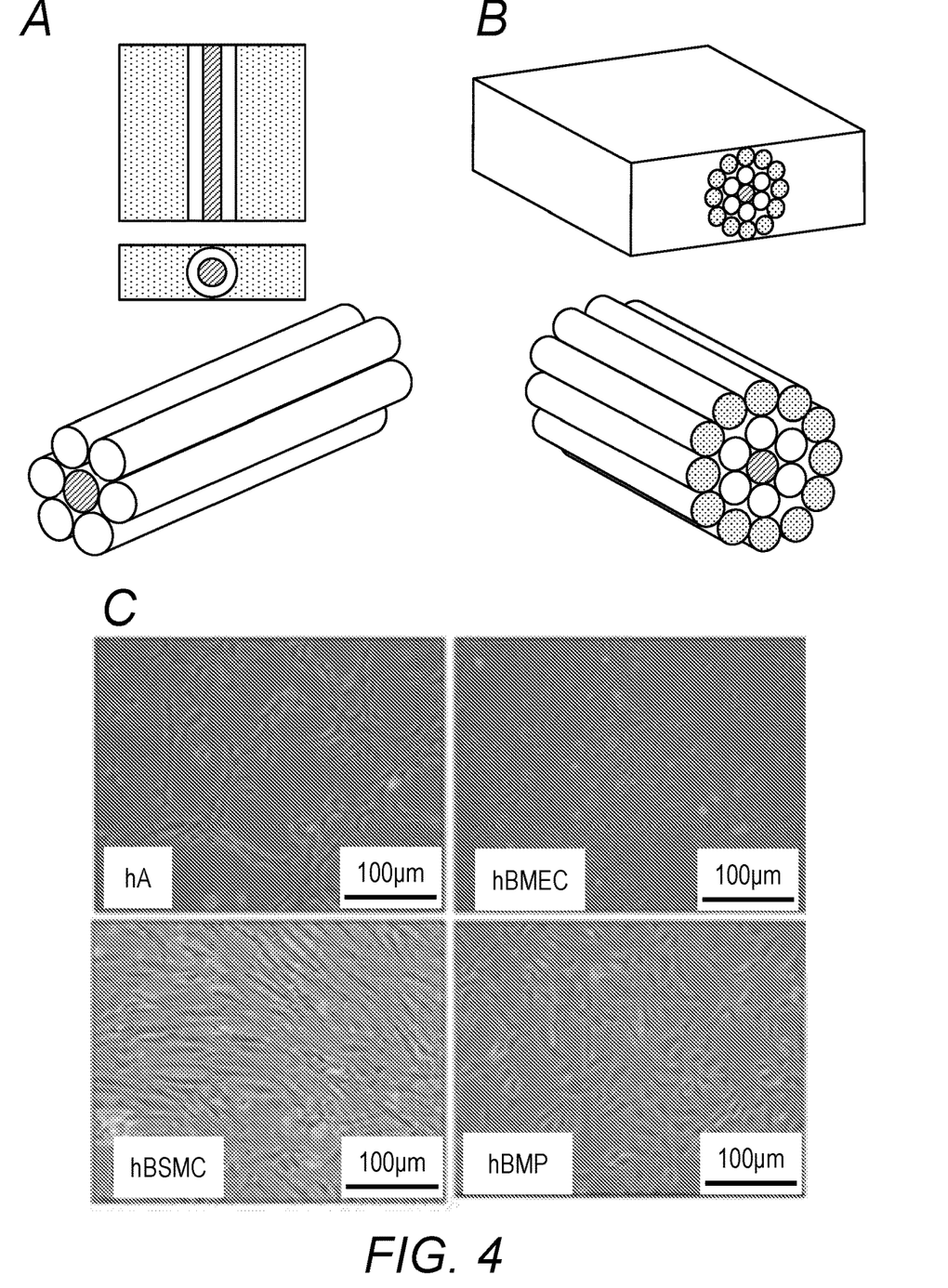
FIG. 4A shows a schematic of a capillary neurovascular unit (NVU). In the center is a sacrificial gelatin lumen containing human brain microvascular endothelial cells (hBMECs) and human brain microvascular pericytes (hBMPs); immediately surrounding the sacrificial gelatin lumen is fibrin gel containing human astrocytes (hAs); and surrounding the fibrin gel containing hAs is fibrin gel with no cells.
FIG. 4B shows a schematic of micro-arteriole NVU. In the center is a sacrificial gelatin lumen with hBMECs; immediately surrounding the sacrificial gelatin lumen is fibrin gel containing hBMPs and hBSMCs; surrounding that fibrin gel is fibrin gel containing hAs and RenCells; and surrounding that fibrin gel is fibrin gel with no cells.
FIG. 4C is a photograph showing primary human cell types in 2D culture that may be used for the constructs.
Figure 5:
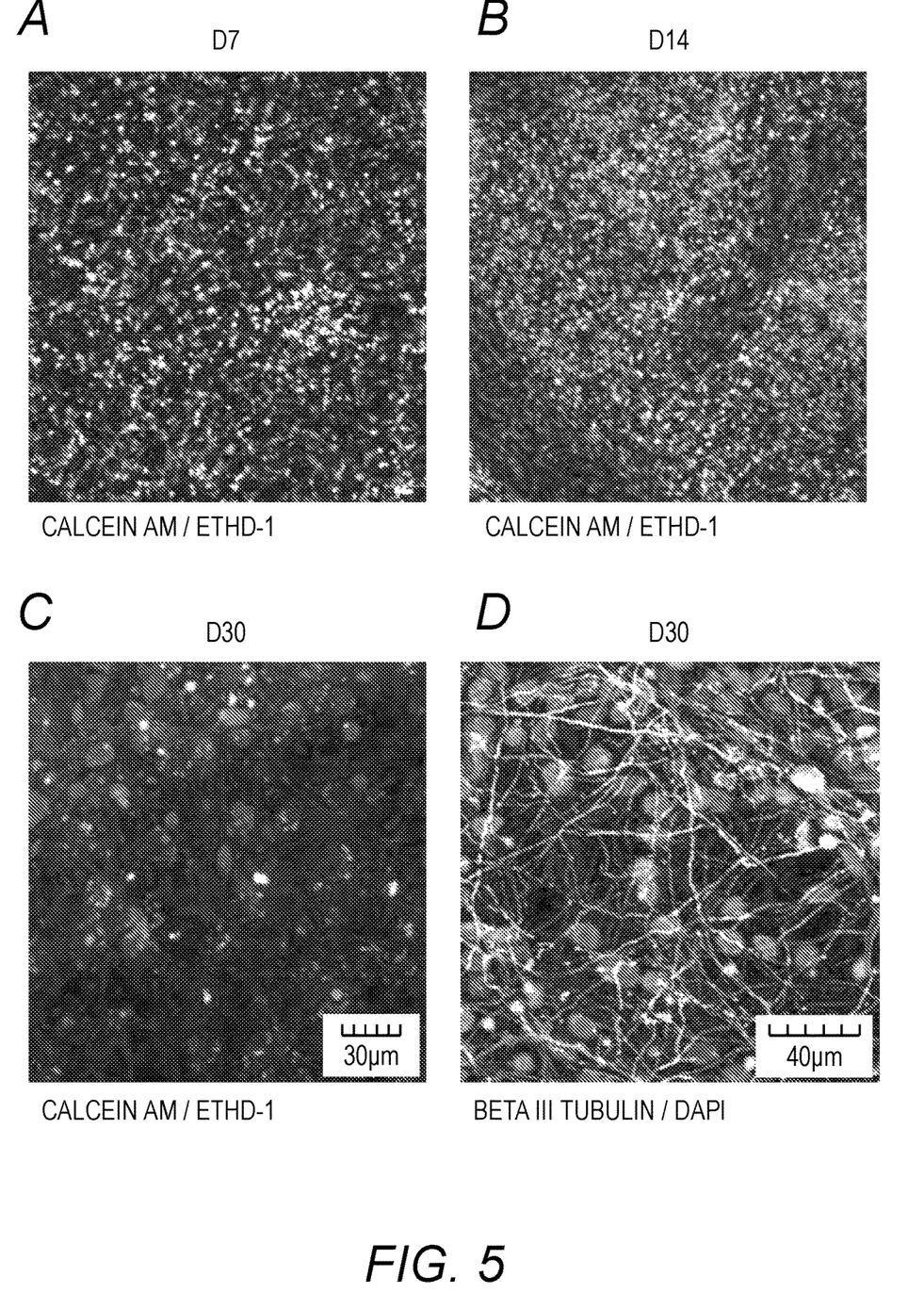
FIG. 5 images demonstrate cell viability of iPSC-derived neuro progenitor cells printed in fibrin gel, cultured in Neural Differentiation media for 72 hrs and Neural maintenance media for up to 50 days. Panels A-C show viability above 95%. The constructs in panel D were immunofluorescence stained for Beta III Tubulin and DAPI was performed to determine cell differentiation and cell nuclei, respectively.

For the cortical tissue unit, 20 million RenCell VM cells (human neural progenitor cells) were reconstituted in fibrin hydrogel and subsequently bioprinted into a silicon mold. For the capillary NVU construct (FIG. 4A), 20 million hAs were integrated into fibrin gel in preparation for microextrusion bioprinting, hBMPs and hBMECs were integrated into gelatin as a sacrificial layer for lumen formation. For the micro-arteriole NVU construct (FIG. 4B), 20 million hAs were integrated into fibrin gel with hBMPs and hBSMCs integrated together into a separate gel. hBMECs were integrated into the gelatin sacrificial layer. Structures were maintained in static culture with endothelial growth media (EGM2, Lonza) exchanged every other day. Printed constructs were fixed at different time points and stained for Beta III tubulin, CD31 and GFAP. On. Day 4 and 7, structures were processed for H&E staining. Immunohistochemistry was performed for the astrocyte marker GFAP and endothelial cell marker CD31. Viability of the printed structure was assessed on Day 10 by way of 2 µM Calcein AM and 4 µM EthD-1 solution.

Figure 6:
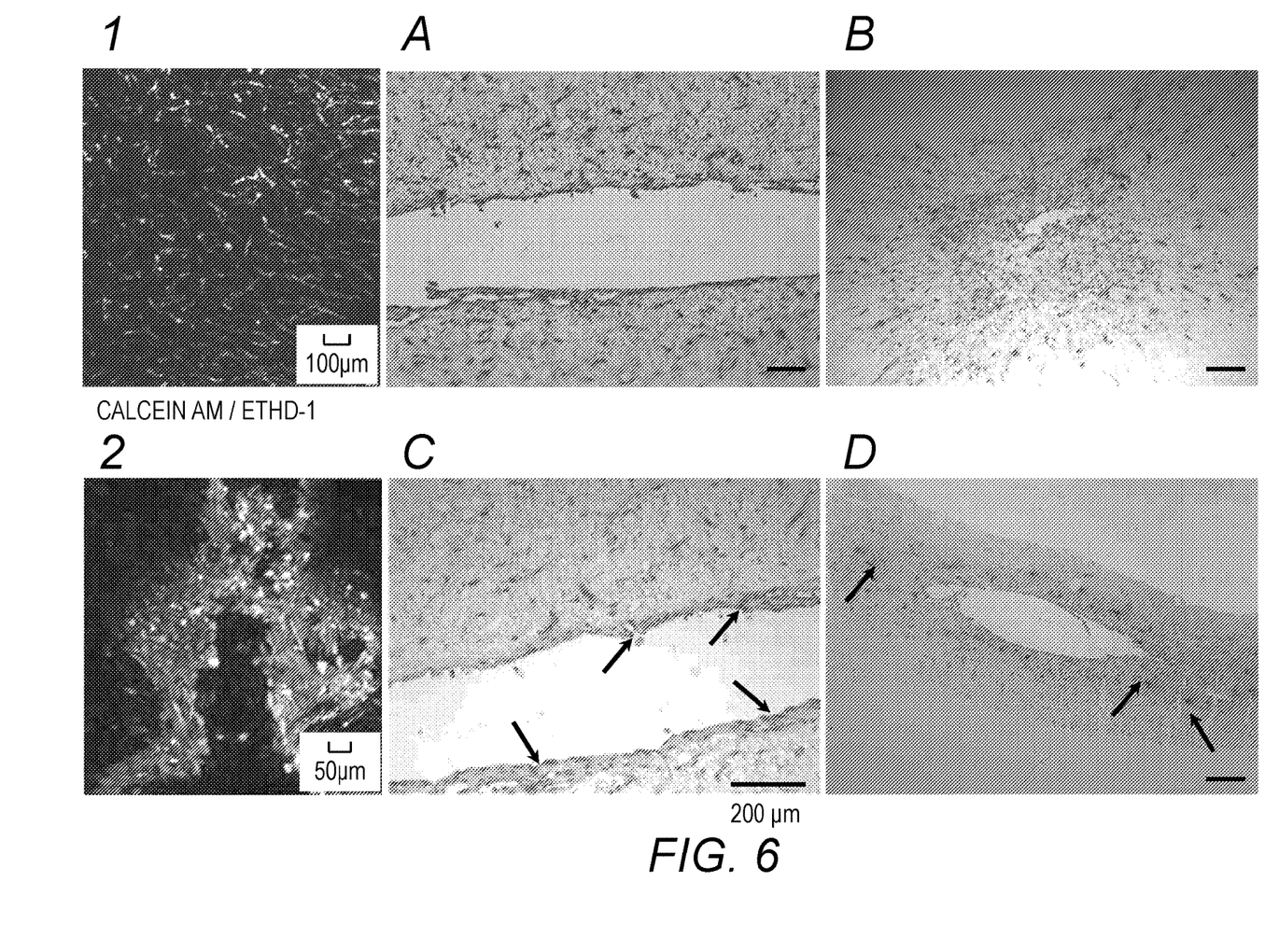
FIG. 6. Panels 1 (top left) and 2 (bottom left) demonstrate cell viability of bioprinted neurovascular units at day 10 and 21, respectively. Image 2 was taken with 2-photon microscope showing cell migration into the lumen. The microvessels were printed in fibrin with Smooth Muscle Cells, Endothelial Cells, Pericytes, Astrocytes and RenCells. Panels A and B: H&E staining of cryosectioned microvessel. In Panel C, the slide was further fixed and, stained for CD31, a marker for endothelial cells staining brown in the lumen shown by arrows. The slide in panel D was prepared as in A,B and subsequently stained for GFAP, astrocyte marker showing the predicted astrocyte localization.

The structures were processed for H&E staining to reveal that they maintained a defined lumen on Day 4 in static culture with cell growth into the lumen on Day 7 (FIG. 6). Immunofluorescence was performed for neuronal differentiation marker, Beta III tubulin, the astrocyte marker GFAP and endothelial cell marker CD31 revealed defined cellular layers on Day 4. Viability assessment on Day 10 revealed over 90% cell viability.

Figure 7:
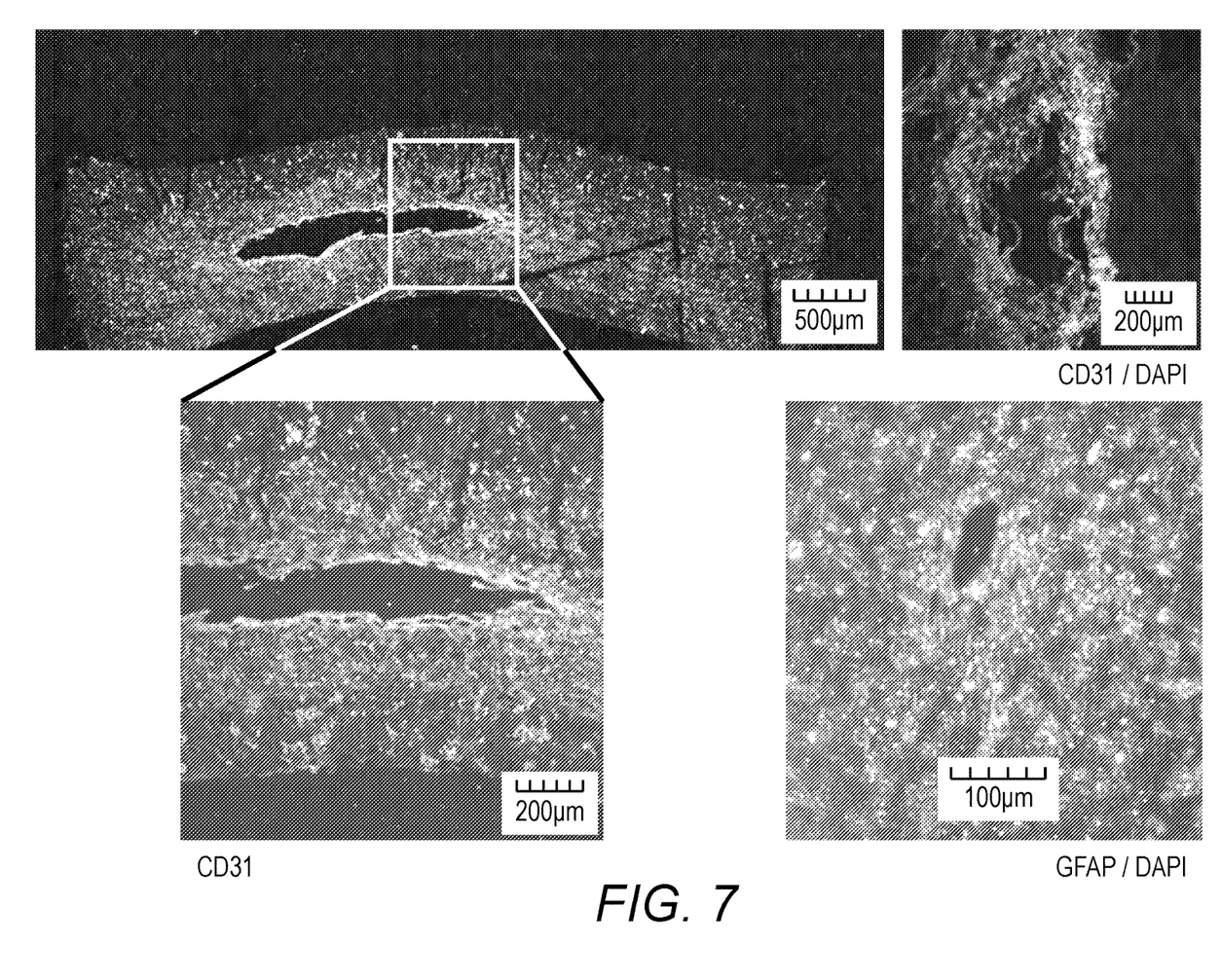
FIG. 7 shows cells of the constructs that were destained using xylene and subsequently immunofluorescence stained for CD31 and GFAP. Even though there is autofluorescence of the fibrin gel, CD31 staining in the lumen is distinct. Transverse sections were stained for GFAP. Bottom right panel shows that GFAP staining was not very distinct; however, destaining was not performed as it may destroy the tissue sample. The lumen is well-defined at day 4. However, occlusion of the lumen is evident by day 7 (top right panel).

The bioprinted NVU constructs reveal cellular layering with a defined lumen present on Day 4. (FIG. 7) immunohistochemistry for endothelial cells and astrocytes show that these cell types are in the expected location on Day 4. Viability assay show high cell viability of the bioprinted cells within the structure, maintained at Day 4. (FIG. 6)

The bioprinted structures are to be placed into dynamic microfluidic culture conditions to assess lumen patency and development of endothelial cell layer tight junction formation.

Bioprinted NVU blood brain barrier is further characterized, and further inclusion of other representative cell types of the human cortex, including neurons, oligodendrocytes, and microglia are performed.

Disease-specific NVU constructs are made with the inclusion of iPSC cell types with known genetic mutations. See Kimbrough, I., et al., Vascular amyloidosis impairs the gliovascular unit in a mouse model of Alzheimer's disease. BRAIN 2015: 138: 3716-3733.

REFERENCES

1. Abbott N J. Inflammatory mediators and modulation of blood-brain barrier permeability. Cellular and molecular neurobiology. 2000; 20(2):131-47, PubMed PMID: 10696506.
2. Armulik A, Genove G, Mae M, Nisancioglu M H, Wallgard Niaudet C, He L, Norlin J, Lindblom P, Strittmatter K, Johansson B R, Betsholtz C. Pericytes regulate the blood-brain barrier. Nature. 2010; 468(7323):557-61. doi: 10.1038/nature09522. PubMed PMID: 20944627.
3. Armulik A, Mae M, Betsholtz C, Pericytes and the blood-brain barrier: recent advances and implications for the delivery of CNS therapy. Ther Deliv. 2011; 2(4):419-22, PubMed PMID: 22826851.
4. Deosarkar S P, Prabhakarpandian B, Wang B, Sheffield J B, Krynska B, Kiani M F, A Novel Dynamic Neonatal Blood-Brain Barrier on a Chip. PLoS One, 2015; 10(11): e0142725. doi: 10.1371/journal.pone.0142725. PubMed PMID: 26555149; PubMed Central PMCID: PMCPMC4640840.
5. Gomes F, Paulin D, Moura Neto V. Glial fibrillary acidic protein (GFAP): modulation by growth factors and its implication in astrocyte differentiation, Brazilian Journal of Medical and Biological Research. 1999; 32(5):619-31.
6. Hutter-Schmid B, Humpel C. Platelet-derived growth factor receptor-beta is differentially regulated in primary mouse pericytes and brain slices. Current neurovascular research. 2016; 13(2):127-34.
7. Drago F, Sautiere P E, Le Marrec-Croq F, Accorsi A, Van Camp C, Salzet M, Lefebvre C, Vizioli J. Microglia of medicinal leech (Hirudo medicinalis) express a specific activation marker homologous to vertebrate ionized calcium-binding adapter molecule 1 (Iba1/alias aif-1). Dev Neurobiol. 2014; 74(10):987-1001. doi: 10.1002/dneu.22179. PubMed PMID: 24723370.
8. Salehi M, Ardeshirylajimi A, Mossahebi-Mohammadi M, Kondori Z, Jorjani M. Oligodendrocyte progenitor cells differentiation of nuclear transferred mouse embryonic stem cells. Cell Mol Biol (Noisy-le-grand), 2015; 61(2): 56-9. PubMed PMID: 26025403.
9. Seok J, Warren H S, Cuenca A G, Mindrinos M N, Baker H V, Xu W, Richards D R, McDonald-Smith G P, Gao H, Hennessy L, Finnerty C C, Lopez C M, Honari S, Moore E E, Minei J P, Cuschieri J, Bankey P E, Johnson J L, Sperry J, Nathens A B, Billiar T R, West M A, Jeschke M G, Klein M B, Gamelli R L, Gibran N S, Brownstein B H, Miller-Graziano C, Calvano S E, Mason Cobb J P, Rahme L G, Lowry S F, Maier R V, Moldawer L L, Herndon D N, Davis R W, Xiao W, Tompkins R G, Inflammation, Host Response to Injury LSCRP. Genomic responses in mouse models poorly mimic human inflammatory diseases. Proc Natl Acad Sci USA. 2013; 110(9):3507-12. doi: 10.1073/pnas.1222878110. PubMed PMID: 23401516; PubMed Central PMCID: PMCPMC3587220.
10. Samanci Y, Samanci B, Sahin E, Altiokka-Uzun G, Kucukali C I, Tuzun E, Baykan B. Neuron-specific enolase levels as a marker for possible neuronal damage in idiopathic intracranial hypertension. Acta Neurol Belg. 2017. doi: 10.1007/s13760-017-0762-2. PubMed PAID: 28220397.
11. Kang H W, Lee S J, Ko I K, Kengla C, Yoo J J, Atala A. A 3D bioprinting system to produce human-scale tissue constructs with structural integrity. Nat Biotechnol. 2016; 34(3):312-9. Pubmed PMID:26878319.

The foregoing is illustrative of the present invention, and is not to be construed as limiting thereof. The invention is defined by the following claims, with equivalents of the claims to be included therein.

That which is claimed is:

1. An in vitro model of a blood brain barrier, said model comprising:

(a) an endothelial cell layer comprising astrocytes, pericytes and endothelial cells, and optionally smooth muscle cells; and
(b) a neuronal cell layer comprising neuronal cells, and optionally oligodendrocytes and/or microglia,
wherein said in vitro model further comprises a porous membrane between said endothelial cell layer and said neuronal cell layer.

2. The in vitro model of claim 1, wherein the neuronal cells comprise primary neuronal cells or neuronal progenitor cells, and optionally wherein said neuronal cell layer is electrically active.

3. The in vitro model of claim 1, wherein the endothelial cells comprise primary endothelial cells or endothelial progenitor cells.

4. The in vitro model of claim 1, wherein the astrocytes comprise primary astrocytes or astrocyte progenitor cells.

5. The in vitro model of claim 1, wherein the pericytes comprise primary pericytes or pericyte progenitor cells.

6. The in vitro model of claim 1, wherein the neuronal cells, endothelial cells, astrocytes and/or pericytes are human.

7. The in vitro model of claim 1, wherein the ratio of astrocytes, pericytes and endothelial cells of the endothelial cell layer is about 3:1:1 by number of cells, respectively.

8. The in vitro model of claim 1, wherein said porous membrane comprises a polymeric material.

9. The in vitro model of claim 1, wherein said endothelial cell layer expresses tight junctions and/or adherens junctions.

10. The in vitro model of claim 1, wherein said endothelial cell layer expresses Zo-1, Claudin-5 and MDR-1.

11. The in vitro model of claim 1, wherein said neuronal cell layer expresses Beta 3 tubulin.

12. The in vitro model of claim 1, wherein said endothelial cell layer is provided in the shape of a blood vessel.

13. The in vitro model of claim 12, wherein said shape is tubular with a hollow center to allow liquid flow therethrough.

14. The in vitro model of claim 12, wherein said neuronal cell layer is situated on the outside of the shape of the blood vessel.

15. A microfluidic device comprising the in vitro model of claim 1, wherein the endothelial cell layer is in fluid contact and/or communication with a liquid.

16. The microfluidic device of claim 15, wherein the neuronal cell layer is in fluid communication with a liquid, and optionally wherein said liquid is different from the liquid in fluid contact and/or communication with the endothelial cell layer.

17. A method of making the in vitro model of a blood brain barrier of claim 1, comprising: depositing the endothelial cell layer on the porous membrane; and depositing the neuronal cell layer on an opposite side of the porous membrane.

18. The method of claim 17, wherein said endothelial cells are microvascular endothelial cells.

19. The method of claim 17, wherein said endothelial cells are human brain microvascular endothelial cells.

20. A method of screening a compound for passage through a blood brain barrier, comprising:
providing the in vitro model of claim 1,
applying the compound to the endothelial layer of the model, and
detecting penetration of the compound through the endothelial layer,
to thereby detect passage of the compound through the blood brain barrier.

21. A method for determining a physiological response to a compound by a blood brain barrier, comprising:
providing the in vitro model of claim 1,
applying the compound to the endothelial layer or the neuronal layer of the model, and
detecting a physiological response from one or more layers,
to thereby determine the physiological response to the compound by the blood brain barrier.

22. The method of claim 21, wherein the physiological response comprises damage, scar tissue formation, infection, cell proliferation, cell migration, burn, cell death, marker release, and/or change in gene expression.

23. The in vitro model of claim 1, wherein said neuronal cell layer comprises neuronal cells, oligodendrocytes and microglia.

24. The in vitro model of claim 1, wherein said endothelial cell layer comprises a self-assembled organoid comprising said astrocytes, pericytes and endothelial cells.

* * * * *

UNITED STATES PATENT AND TRADEMARK OFFICE
CERTIFICATE OF CORRECTION

| | |
|---|---|
| PATENT NO. | : 11,230,702 B2 |
| APPLICATION NO. | : 16/322232 |
| DATED | : January 25, 2022 |
| INVENTOR(S) | : Wicks et al. |

It is certified that error appears in the above-identified patent and that said Letters Patent is hereby corrected as shown below:

In the Specification

Column 10, Line 54: Please correct "BEE" to read -- BBB --

Signed and Sealed this
Twenty-eighth Day of June, 2022

*Katherine Kelly Vidal*

Katherine Kelly Vidal
*Director of the United States Patent and Trademark Office*